United States Patent
Dicarlo et al.

(10) Patent No.: US 6,839,088 B2
(45) Date of Patent: Jan. 4, 2005

(54) SYSTEM AND METHOD FOR ESTIMATING PHYSICAL PROPERTIES OF OBJECTS AND ILLUMINANTS IN A SCENE USING MODULATED LIGHT EMISSION

(75) Inventors: Jeffrey M. Dicarlo, Sunnyvale, CA (US); Peter B. Catrysse, Palo Alto, CA (US); Feng Xiao, Stanford, CA (US); Brian A. Wandell, Menlo Park, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 673 days.

(21) Appl. No.: 09/874,881

(22) Filed: Jun. 4, 2001

(65) Prior Publication Data

US 2002/0171842 A1 Nov. 21, 2002

Related U.S. Application Data

(60) Provisional application No. 60/280,646, filed on Mar. 31, 2001.

(51) Int. Cl.⁷ ............................................. H04N 5/222
(52) U.S. Cl. .................................. 348/370; 348/223.1
(58) Field of Search ............................. 348/370, 371, 348/223.1

(56) References Cited

U.S. PATENT DOCUMENTS

| | | | | |
|---|---|---|---|---|
| 5,081,530 A | * | 1/1992 | Medina | 348/46 |
| 5,548,398 A | | 8/1996 | Gaboury | 356/218 |
| 6,069,972 A | | 5/2000 | Durg et al. | 382/167 |
| 6,081,076 A | * | 6/2000 | Ogawa | 315/241 P |
| 6,122,042 A | * | 9/2000 | Wunderman et al. | 356/73 |
| 6,505,002 B2 | * | 1/2003 | Fields | 396/287 |
| 6,777,684 B1 | * | 8/2004 | Volkov et al. | 250/341.1 |

OTHER PUBLICATIONS

Shigeru Ando, Takuya Nakamura, and Takaaki Sakaguchi; "Ultrafast correlation image sensor: concept, design, and applications;" Proc. IEEE CCD/AIS Workshop, Bruges, Belgium (1997).

Shigeru Ando and Akira Kimachi; "Time–Domain correlation image sensor: first CMOS realization of demodulator pixels array;" Proc. IEEE CCD/AIS Workshop, Karuizawa, Japan (1999).

* cited by examiner

Primary Examiner—Wendy R. Garber
Assistant Examiner—Jacqueline Wilson
(74) Attorney, Agent, or Firm—Lumen Intellectual Property Services, Inc.

(57) ABSTRACT

Color balancing algorithms for digital image processing require an accurate estimate of the physical properties of the ambient scene illuminant, particularly its spectral power distribution. An active imaging method and apparatus estimate these properties by emitting modulated light with a known spectral power distribution into a region of a scene. Backscattered light is detected and demodulated to separate output representing active emitter light from output representing ambient illuminant light. Using the emitter-related detector output and the known emitter spectral power distribution, the surface spectral reflectance function of the illuminated scene region can be computed. Subsequently, the spectral power distribution of the ambient scene illuminant can be computed from the surface reflectance function and the illuminant-related output of the detector. The estimated spectral power distribution can be used in standard color balancing algorithms for digital or film images.

28 Claims, 4 Drawing Sheets

Prior Art

SYSTEM AND METHOD FOR ESTIMATING PHYSICAL PROPERTIES OF OBJECTS AND ILLUMINANTS IN A SCENE USING MODULATED LIGHT EMISSION

CROSS-REFERENCE TO RELATED APPLICATIONS

This application claims the benefit of U.S. Provisional Application No. 60/280,646, filed Mar. 31, 2001, which is herein incorporated by reference.

FIELD OF THE INVENTION

This invention relates generally to photography and imaging and to the processing of color images to achieve an accurate and pleasing color appearance. More particularly, it relates to a system and method for estimating physical properties of objects and illuminants in a scene for color balancing, color correction, and other aspects of image processing of still and motion photography.

BACKGROUND ART

Images acquired by either film or digital cameras are enhanced through processing of the image color using a number of complex algorithms. The goal of these algorithms is to render an image reproduction that is pleasing and has the same color appearance as the objects in the original scene. The performance of all of these algorithms is substantially improved when the physical properties of objects and/or illuminants in the scene are known.

For example, color balancing is one important image processing algorithm. Color balancing refers to the act of adjusting the image colors to correct for distortions in color appearance when the image is acquired under one illuminant but rendered under a second, different illuminant. Say an image of a scene is captured indoors under a tungsten ambient illuminant. The unprocessed image will have a yellowish appearance (color cast) when viewed under natural outdoor ambient illumination. The performance of color balancing algorithms can be improved when the ambient illuminant of the scene is known.

Because of its importance, there has been a great deal of academic and industrial research on illuminant estimation. State-of-the-art ambient illuminant estimation algorithms include gray-world, specular reflections, physical-realizability, color-by-correlation, and Bayesian color constancy algorithms. All of these algorithms work in a passive mode: the algorithms estimate the ambient illuminant using light collected passively by film or a digital image sensor. In passive mode algorithms, the collected and analyzed light originates from the ambient illuminant and is already being collected for imaging purposes. For example, U.S. Pat. No. 6,069,972, issued to Durg et al., discloses a method for white balancing a digital color image. Using the captured image, color components of the pixels are analyzed to determine a global white point and perform color balancing on the entire image.

The most widely known and implemented of these passive mode algorithms is the gray-world algorithm, described in G. Buchsbaum, "A Spatial Processor Model for Object Color Perception," *J. Franklin Institute*, 310, 1-26 (1980); and R. W. G. Hunt, *The Reproduction of Color*, $5^{th}$ ed, Fountain Press, England (1996). The gray-world algorithm assumes that the average surface reflectance of objects in a scene corresponds to a gray surface. Based on this assumption, the algorithm uses the average color of an image as a measure of the ambient illumination.

Color-by-correlation is a more recent and novel passive mode illuminant estimation algorithm, described in G. D. Finlayson, P. M. Hubel, and S. Hordley, "Color by Correlation,"Proceedings of the IS&T/SID $5^{th}$ *Color Imaging Conference: Color Science, Systems, and Applications*, Scottsdale, Ariz., 6-11 (1997). The method assumes that the number of possible ambient illuminants encountered is quite small. The algorithm tests which of the possible illuminants is the most likely one given the image data. Color-by-correlation does this test by comparing the chromaticity gamut of the image with the chromaticity gamut of each assumed illuminant multiplied by a database of natural surface reflectance functions. The algorithm simply picks the ambient illuminant whose gamut most overlaps the image gamut.

In another interesting algorithm, disclosed in U.S. Pat. No. 5,548,398, issued to Gaboury, a temporal sensor is included to detect the flicker frequency of the passive illumination. Steady illuminants are likely to be from natural sources, such as the sun, whereas artificial illuminants, such as fluorescent lights, flicker at known frequencies (typically 60 or 120 Hz).

By detecting this temporal frequency, the system can make an improved guess at the likely illuminant type and color.

Passive mode algorithms use image data that depend simultaneously on the ambient illuminant and the object surface reflectance functions. In order to derive an estimate of the ambient illuminant from image data, the algorithms must make assumptions about the properties of the object surface reflectance functions. There is no way to verify that these assumptions are true.

Active imaging methods (AIMs) differ from passive algorithms: they emit a signal into a scene. An example of an AIM system is a sonar range finder used for auto-focusing. The time-of-flight for the signal to leave the camera and return is measured and used to specify the distance to an object in the scene. This distance is used to set the camera focus. For more information on auto-focus algorithms, see G. Ligthart and F.C.A. Groen, "A Comparison of Different Autofocus Algorithms," *Proc. of IEEE Int. Conf on Pattern Recognition* (1982). Range scanning systems emit laser pulses or other signals into a scene to determine the distance and shape of three-dimensional objects; for example, see P. Besl, "Active, Optical Range Imaging Sensors" *Machine Vision and Applications*, 1, 127-152 (1988).

Active imaging methods have not been applied to estimating physical properties relating to color. All existing color balancing methods are passive and therefore require estimation of physical properties that cannot be confirmed by measurement, thereby limiting the accuracy of the methods.

OBJECTS AND ADVANTAGES

Accordingly, it is a primary object of the present invention to provide an apparatus that emits modulated light into a region of a scene and captures a sequence of measurements (active measurements). It is an additional object to use the measurement sequence to calculate the physical properties of objects and illuminants in the region. These properties are stored for use in subsequent analyses.

It is another object of the invention to provide a method to distinguish between illuminant and object properties within a region of a scene. Illuminant properties are any properties that are related to the spectral power distribution of the illuminant, and object properties are any properties that are related to the spectral surface reflectance function of the object.

It is a specific advantage of the invention to use the active measurements to guide the color balance of an acquired digital or film image. In this way, a pleasing reproduction of the original scene is created with the same color appearance as that of the objects in the original scene.

SUMMARY

These objects and advantages are attained by an active imaging method (AIM) and apparatus designed to measure physical properties of illuminants and objects within a region of a scene. The AIM system can be used to enhance the performance of imaging systems that perform color balancing and other image processing algorithms. Using a temporally or spatially modulated emitted light, the AIM system can produce images that depend only on the AIM emitter despite the presence of a steady ambient illumination. From these images, it is possible to estimate accurately important scene properties including object surface reflectance and ambient illumination.

Specifically, the present invention provides a method for estimating physical properties of a scene that includes a scene object illuminated by a scene illuminant. The scene is illuminated with, say, a temporally modulated light from an emitter; backscattered light from the scene is detected with a detector in a sequence of temporal measurements; and output from the detector is analyzed to distinguish between light originating from the emitter (emitter output) and light originating from the scene illuminant (illuminant output). The temporal modulation pattern of the emitter is known and differs from the ambient scene illuminant. Hence, the signal caused specifically by the emitter can be extracted from the measurement sequence by determining the response corresponding to the known temporal modulation.

Based on the emitter output from the detector and a known spectral power distribution of the emitter, object properties in the region under emitter illumination are estimated. For example, the spectral surface reflectance function of a scene object and related properties can be determined. From the estimated object properties, physical properties of the scene illuminant, such as its spectral power distribution, are then determined using the illuminant output. An image of the scene is produced either from illuminant output of the detector or from an independent detector. Estimated illuminant information is stored and associated with the image for use in subsequent color image processing of the image data; for example, color balancing is performed on the image using the determined spectral power distribution of the scene illuminant.

The invention also provides an apparatus for imaging a scene containing a scene object illuminated by a scene illuminant. The apparatus contains an emitter, which can be any light-emitting device such as a laser, light-emitting diode, or flash, for emitting modulated light such as temporally modulated light; and a detector, which can be any device that can measure light reflected from a scene or object, for example, an image sensor or photodetector. The apparatus also contains processing means for analyzing output from the detector to distinguish between output from the illuminant and output from the emitter, and for estimating object properties of the scene object based on the emitter output and a known spectral power distribution of the emitter. Object properties are typically any properties related to a spectral surface reflectance function of the scene object. Preferably, the apparatus also includes processing means for estimating physical properties of the scene illuminant, properties related to a spectral power distribution of the scene illuminant, based on the object properties. The apparatus also preferably contains processing means for performing color balancing on an image of the scene using the estimated scene illuminant properties.

DETAILED DESCRIPTION

Although the following detailed description contains many specifics for the purposes of illustration, anyone of ordinary skill in the art will appreciate that many variations and alterations to the following details are within the scope of the invention. Accordingly, the following preferred embodiment of the invention is set forth without any loss of generality to, and without imposing limitations upon, the claimed invention.

The present invention provides an active imaging method (AIM) for measuring physical properties of illuminants and objects in a scene. Unlike prior art methods that attempt to estimate illuminant properties from a captured image of the scene, the present invention actually measures the spectral surface reflectance function of scene objects and then uses this function to estimate the spectral power distribution of the scene illuminant. Any subsequent standard image processing performed using the measured illuminant spectral power distribution is therefore much more accurate than with prior art methods.

Figure 1:
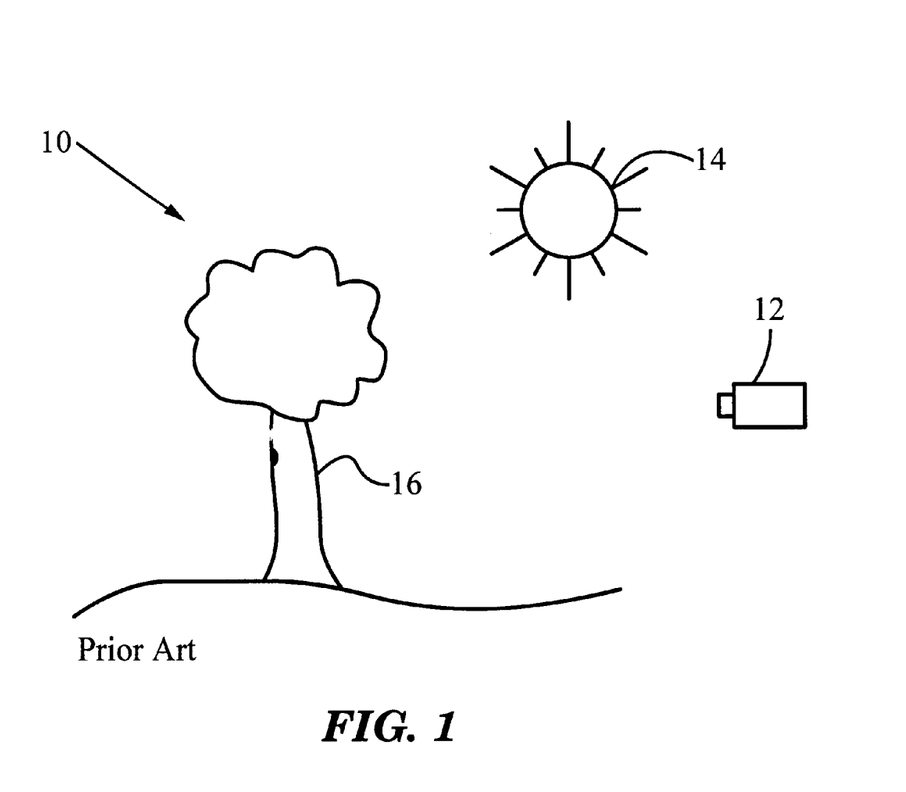
FIG. 1 (prior art) illustrates image capture of a scene including a scene object illuminated by an ambient scene illuminant.

FIG. 1 illustrates image capture of a scene 10 using a prior art image capture device 12, for example, a digital camera. An ambient illuminant 14, in this case the sun, illuminates an object 16, and an image is captured by device 12 of illuminated object 16. Device 12 typically contains a planar detector array for acquiring images and processors for performing demosaicing, image compression, color balancing, and other processing of acquired images. Device 12 also contains a memory for storing the captured and processed images and related data. Preferably, the image is captured as a color, multiple bit per pixel image. For still cameras, the color format is usually RGB (red, green, blue), although the present invention is applicable to any color format.

Scene 10 includes scene illuminant 14 and scene object 16. Scene illuminant 14, also referred to as a passive or ambient illuminant, is described by a spectral power distribution $P(x,\lambda,t)$, where x is position, $\lambda$ is wavelength, and t is time. $P(x,\lambda,t)$ (or some related quantity) represents the power emitted by the illuminant over a range of wavelengths and is needed to perform accurate color balancing of the acquired image. Scene object 16 is described by a spectral surface reflectance function $S(x,\lambda,)$. The color signal, $C(x, \lambda, t) = S(x,\lambda)P(x,\lambda,t)$, which refers to the spectral power distribution of ambient light arriving at the human eye or image sensor in device 12 after reflection at the surface of object 16, is computed by multiplying the ambient illuminant spectral power distribution by the spectral surface reflectance of the object. Thus, in principle, if two of these three quantities are known, the third can be estimated.

The active imaging method (AIM) of the present invention provides a means for estimating the physical properties of illuminants and objects within a region of a scene. Physical properties of illuminants are any properties that are related to the spectral power distribution of the illuminant, and physical properties of objects are any properties that are related to the spectral surface reflectance function of the object. Any one of a number of standard color formats can be used to represent the wavelength dependency of the surface reflectance function and spectral power distribution. Various formats include:

- RGB (red, green, blue), typically used for digital cameras and displays;
- CMYK (cyan, magenta, yellow, black), used for color printing;
- HSB (hue, saturation, and brightness), also known as HLS (hue, luminance, and saturation);
- YIQ (luminance, in-phase, quadrature), a color space derived from the NTSC television color standard;
- YUV (luminance, blue, red), a color space derived from the PAL television color standard;
- Linear models using basis functions;
- Polynomial models; and
- Manifold models, which are extensions of linear models.

Any digital color format representation of the surface reflectance function and spectral power distribution are referred to herein as properties related to the surface reflectance function or spectral power distribution, respectively. It is to be understood that any representation of these quantities, including representations not explicitly mentioned, is within the scope of the present invention.

Figure 2:
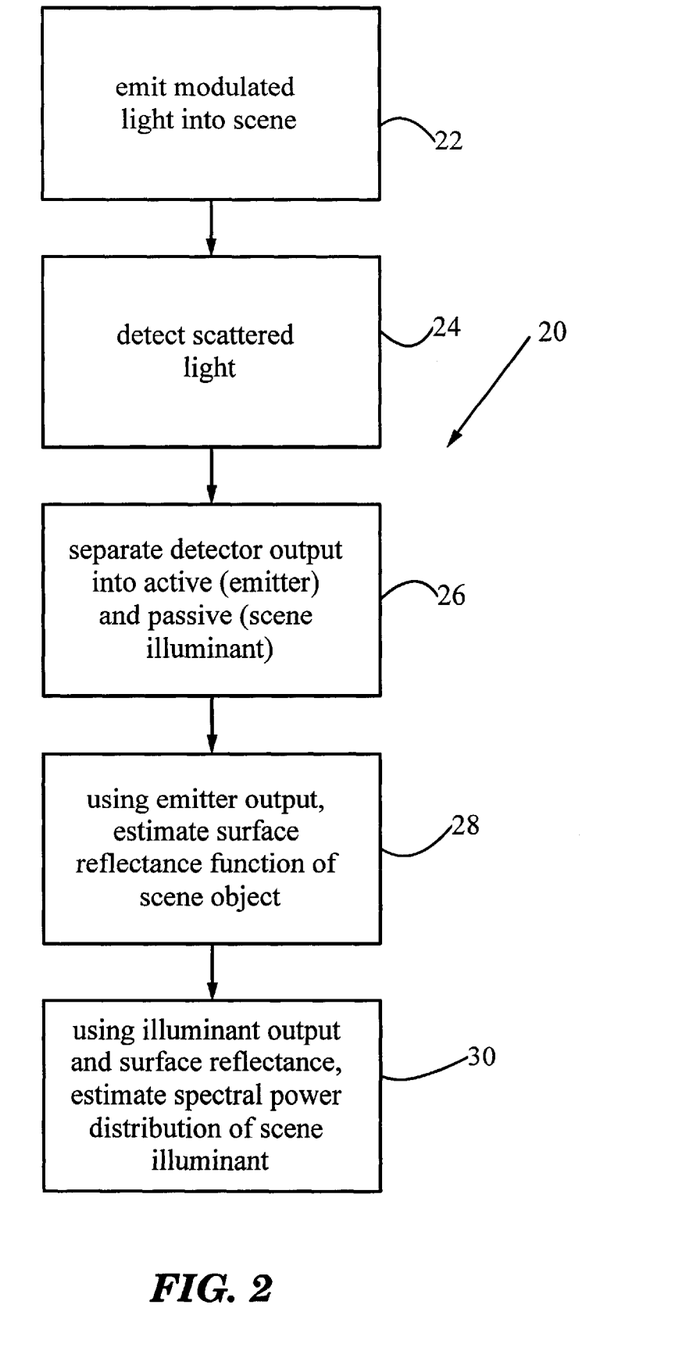
FIG. 2 is a flow diagram of a method of the invention for estimating object properties and illuminant properties of objects and illuminants in a scene.
Figure 3:
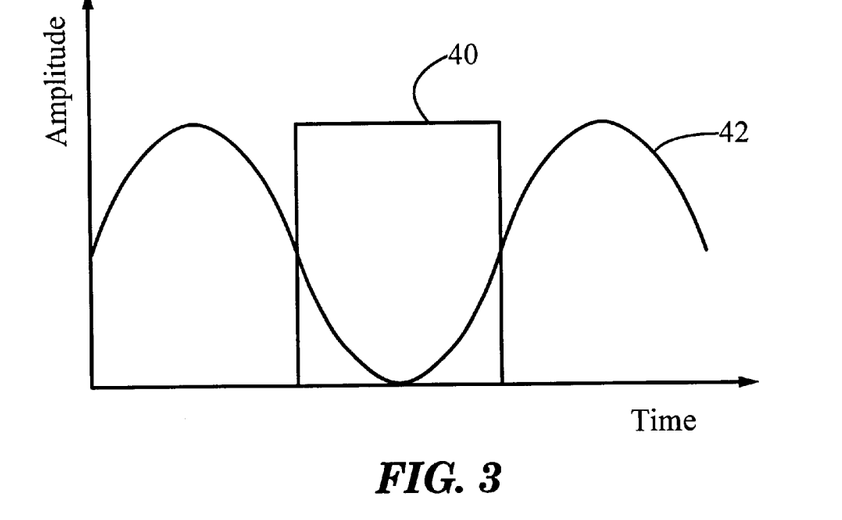
FIG. 3 is a graph of two possible temporal modulation functions of an emitter of the present invention.
Figure 4:
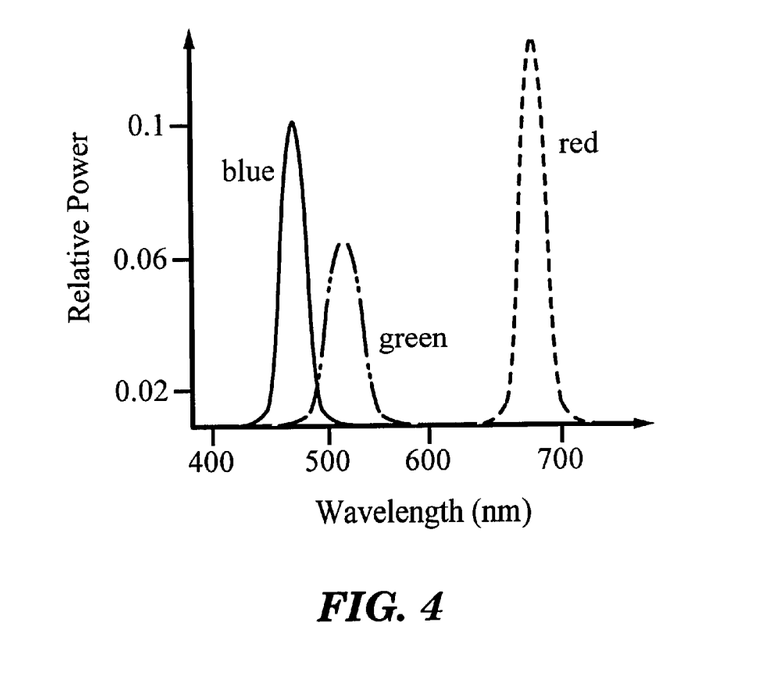
FIG. 4 is a graph of spectral power distributions of three active emitter illuminants.

FIG. 2 shows a flow diagram of a method 20 of the present invention for estimating physical properties of objects and illuminants of a scene. In step 22, modulated light is emitted into a region of the scene using an emitter, also referred to as an active illuminant. In a preferred embodiment, the emitted light is temporally modulated; alternatively, spatial modulation can be used. The remainder of this description refers to temporal modulation for illustration purposes. However, it is to be understood that other types of modulation fall within the scope of the present invention. Temporally modulated light has its amplitude modulated in time according to a known function. Any modulation function can be used, such as a square wave or sinusoidal modulation, but the modulation function should be different from the modulation function of the scene illuminant. For example, an indoor illuminant typically flickers at a frequency of 60 or 120 Hz, and so the modulation function should not contain significant energy at these frequencies. Further design considerations for the modulation function are discussed below. FIG. 3 illustrates two possible modulation functions, a square wave 40 (on-off) and a sinusoidal function 42. Preferably, the emitter contains multiple active illuminants, each with a different temporal modulation function. Both the temporal modulation and the spectral power distribution of the light emitted by the emitter must be predetermined, because they are required for subsequent processing. FIG. 4 illustrates spectral power distributions of three sample emitter illuminants, red, green, and blue light-emitting diodes.

In step 24, a detector acquires a sequence of temporal measurements of light backscattered from the scene object, which is illuminated by both the emitter (active illuminant) and the scene illuminant, also known as a passive illuminant. The detector is typically an array of photodetectors capable of detecting color according to a particular color format. Each photodetector in the array produces output related to the number of photons detected. The output of the detector represents photons backscattered from the scene object and originating from both the emitter and the scene illuminant. Emitter output is output representing light originating only from the emitter, while illuminant output is output representing light originating only from the passive illuminant. Note that steps 22 and 24 occur simultaneously; reflected light is detected while the emitter is emitting modulated light.

In step 26, the temporal measurements of each detector pixel are analyzed to separate emitter output from illuminant output, as discussed below. The outputs can be separated because the temporal modulation of the emitter light, and therefore the emitter output, is different from the temporal modulation of the scene illuminant. The scene illuminant is either steady or modulated at a known frequency, e.g., 60 or 120 Hz, while the emitter is modulated according to the predetermined modulation function. Step 26 is performed using standard demodulation and filtering techniques known in the art. Suitable demodulation techniques are described in H. Taub and D. L. Schilling, *Principles of Communication Systems* ($2^{nd}$ ed.), New York: McGraw-Hill (1986); and R. E. Ziemer and W. H. Tranter, *Principles of Communications: Systems, Modulation and Noise* ($3^{rd}$ ed.), Boston: Houghton Mifflin (1990); both of which are herein incorporated by reference. The emitter output and properties computed from it are referred to as the active measurements. The illuminant output and images obtained from it are referred to as the passive measurements.

In step 28, the emitter output and the known spectral power distribution of the emitter are used to estimate the surface reflectance function of the region illuminated by the emitter. There are many standard techniques for estimating the surface reflectance function based on an image sensor response and illuminant properties; for example, see B. K. P. Horn, "Exact reproduction of colored images," *Computer Vision, Graphics and Image Processing*, 26, 135-167 (1984); and B. A. Wandell, "The synthesis and analysis of color images," *IEEE PAMI*, PAMI-9, 2-13 (1987); both of which are herein incorporated by reference.

The estimated spectral surface reflectance function is used in step 30, along with the illuminant output extracted in step 26, to estimate the spectral power distribution of the scene illuminant in the region under emitter illumination. Step 30 is similar to step 28 and uses the same standard techniques. However, in this case, the spectral surface reflectance function is known, while the spectral power distribution is being estimated. The estimated illuminant spectral power distribution is stored and associated with an image obtained under scene illuminant only (a passive measurement) for subsequent processing. For example, standard color balancing algorithms require an estimation of the spectral power distribution of the illuminant. The illuminant spectral power distribution obtained using the present invention can be incorporated into any such standard algorithm.

A key feature enabling the present invention is the ability to separate the photons returned from the steady ambient illuminant (passive or scene illuminant) from the photons returned from the emitter (active illuminant). Because the emitter light is temporally modulated using a predetermined modulation function, the detector output can be separated. Ando et al. describe experiments with a monochrome CMOS sensor that uses time-domain correlation coupled with monochrome illuminant modulation (S. Ando and A. Kimachi, "Time-Domain Correlation Image Sensor: First CMOS Realization of Demodulator Pixels Array," *Proc. IEEE CCD/AIS Workshop*, Karuizawa, Japan (1999); and S. Ando, K. Nakamura, and T. Sakaguchi, "Ultrafast Correlation Image Sensor: Concept, Design, and Applications," *Proc. IEEE CCD/AIS Workshop*, Bruges, Belgium (1997)). In their method, a sensor performs multiple image captures and then calculates a single image representing the scene as if it were illuminated by the modulated light source alone. They have shown that demodulation of active and passive illuminants is possible for monochrome sensors. However, their applications of interest are significantly different from those of the present invention, and they have not extended their techniques to color imaging. For experimental evidence of active color imaging methods implemented by the present inventors, see F. Xiao, J. M. DiCarlo, P. B. Catrysse, and B. A. Wandell, "Image analysis using modulated light sources," *Proceedings of the SPIE, Image Sensors*, San Jose, Calif., January 2001, herein incorporated by reference.

Demodulation of active (emitter) and passive (scene illuminant) color illuminants is straightforward. Consider a small surface patch of a scene object at a position x. The total illuminant spectral power distribution at location x is the sum of the active illumination, $A(x,\lambda,t)$, which is known, and the passive illumination, $P(x,\lambda,t)$, that is present in the environment and to be determined. The active illuminant can itself be a sum of N multiple active illuminants $A_i(x,\lambda, t)$. The total illumination at a location x is given by $$E(x, \lambda, t) = P(x, \lambda, t) + A(x, \lambda, t) \quad (1)$$
$$= P(x, \lambda, t) + \sum_{i=0}^{N} A_i(x, \lambda, t)$$
$$= P(x, \lambda, t) + A_o(x, \lambda) + \sum_{i=1}^{N} A_i(x, \lambda, t).$$

$A_o$ is the mean level of the sum of the active illuminants and is constant over time. The $A_i$ terms are modulations of the active illuminants about this mean level. In most cases, the passive illumination does not change over time, so that $P(x,\lambda,t)=P(x,\lambda)$. Consequently, equation (1) becomes $$E(x, \lambda, t) = (P(x, \lambda) + A_o(x, \lambda)) + \sum_{i=1}^{N} A_i(x, \lambda, t). \quad (2)$$

It is desirable to arrange the modulation of the active illuminants so that their relative spectral composition is unchanged as the intensity modulates. This results in further simplification of the modulating term:

$$E(x, \lambda, t) = (P(x, \lambda) + A_o(x, \lambda)) + \sum_{i=1}^{N} A_i(x, \lambda) F_i(t). \quad (3)$$

The modulation control functions $F_i(t)$ are preferably chosen to be orthogonal to each other to allow separation of the reflected light originating from different active illuminants. Note that all of the $A_i$ functions have a zero mean, because the mean was separated into the $A_o$ term. Thus $$\int F_i(t)F_j(t)dt = \delta_{i,j}, \text{ where } \delta_{i,j} = \begin{cases} 1, i = j \\ 0, i \neq j \end{cases} \quad (4)$$

and $$\int F_i(t)dt = 0.$$

Now consider the response of an ideal detector with spectral sensitivity $R(\lambda)$ measuring light scattered from a surface patch with reflectance $S(x,\lambda)$. The response of the detector is $$r(x,t)=\int R(\lambda)E(x,\lambda,t)S(x,\lambda)d\lambda. \quad (5)$$

The temporal output of the detector can be demodulated to calculate the output associated with each modulated light source. The $i^{th}$ demodulated image $r_i(x)$ (i.e., the $i^{th}$ emitter output) is found from the inner product of the detector response $r(x,t)$ and the $i^{th}$ modulation control function:

$$r_i(x)=\int r(x,t)F_i(t)dt. \quad (6)$$

Substituting equation (5) into equation (6) leads to $$r_i(x)=\int R(\lambda)S(x,\lambda)\int E(x,\lambda,t)F_i(t)d\lambda dt. \quad (7)$$

Substituting equation (3) into equation (7) and using equation (4) to simplify, equation (7) becomes:

$$r_i(x)=\int R(\lambda)S(x,\lambda)A_i(x,\lambda)d\lambda. \quad (8)$$

Hence the $i^{th}$ demodulated image $r_i(x)$ depends only on the detector response, the spectral surface reflectance of the scene object, and the light emitted by the $i^{th}$ emitter. It will be apparent to one skilled in image processing how to compute the inner product between the detector response and each modulation control function using software or hardware means to obtain $r_i(x)$. From $r_i(x)$ and knowing $R(\lambda)$ and $A_i(x,\lambda)$, $S(x,\lambda)$ can be computed using one of the methods mentioned above. Although estimating the surface reflectance requires only one emitter illuminant, multiple active illuminants improve accuracy of the estimated value.

In the absence of noise and system considerations, all sets of orthogonal control functions with equal energy provide equivalent performance. While the present invention may be implemented using any modulation control functions, different functions are optimal under different conditions. Factors influencing the selection of functions include ease of synchronizing active illuminants and image acquisition devices, hardware capabilities, scene characteristics, and system noise and quantization characteristics.

For example, some control functions do not require the modulator and demodulator to be accurately synchronized, which may be desirable in circumstances in which the emitter controller and detector are not closely coupled. Sinusoidal function 42 (FIG. 3), for example, can be demodulated without precise synchronization between the detector and emitter. Square wave function 40, however, requires the detector and emitter to be accurately synchronized to avoid image acquisition during the on/off transition.

The noise properties of the entire system should also be considered in selecting control functions. If the main system noise is from quantization, with all other sources negligible, then sinusoidal functions outperform square wave functions, particularly if many active images are acquired. With sinusoidal functions, the quantization noise is more evenly distributed about zero, and so the error tends to average to zero. Appropriate considerations apply to other noise sources.

Figure 5:
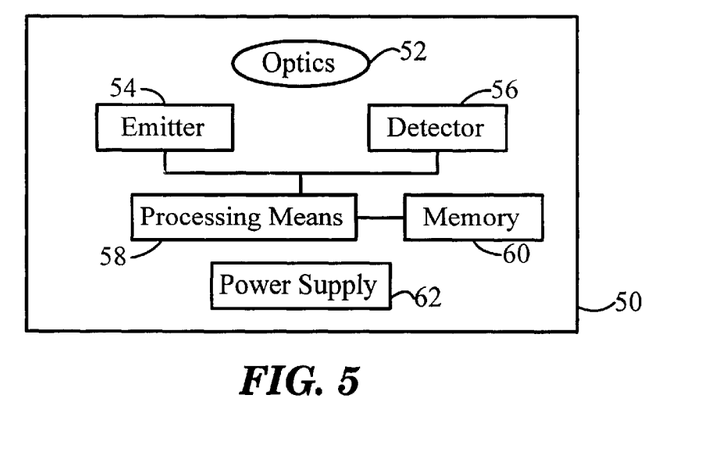
FIG. 5 is a block diagram of an image capture apparatus of the present invention.

A preferred embodiment of an active imaging apparatus 50 according to the present invention is shown schematically in FIG. 5. Apparatus 50 contains optics 52, an emitter 54, a detector 56, processing means 58, a memory 60, and a power supply 62. Although these components are shown separately, they can be integrated together in any combination. Emitter 54, detector 56, and processing means 58 implement the core of the active imaging method of the present invention. Apparatus 50 is preferably implemented as a digital camera and therefore requires only an emitter 54 and some additional processing means 58 (and potentially an additional detector 56, as discussed below) to be added to the components of existing digital cameras.

Optics 52 collimate light from emitter 54 and image reflected light from the scene onto detector 56. Any suitable optical configuration can be used. Power supply 62 provides power to emitter 54, detector 56, processing means 58, memory 60, and optics 52 (if necessary for focusing). Power supply 62 is typically a battery, but may be any type of power source. Memory 60 stores acquired images and related data, such as the estimated spectral power distribution of the scene illuminant. Optics 52, memory 60, and power supply 62 are necessary to enable a working system but function only as support hardware for emitter 54, detector 56, and processing means 58.

Figure 6:
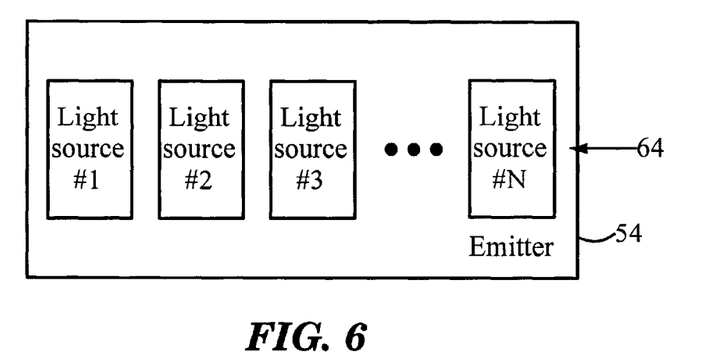
FIG. 6 is a block diagram of an emitter of the apparatus of FIG. 5.

Emitter 54 is any light-emitting device containing one or more illuminants with known spectral power distribution. Examples of possible emitters include but are not limited to lasers, light-emitting diodes, and flashes. Preferably, emitter 54 emits temporally modulated light into only a small region of the scene. FIG. 6 is a schematic block diagram of emitter 54, which preferably contains multiple active illuminants 64, each with a known spectral power distribution. Any number of illuminants, including only one, and any broad- or narrow-band spectral power distributions may be used in emitter 54. Typical methods for estimating surface reflectance of the scene object use broad-band basis functions for efficient computational representation of the surface reflectance function. Using broad-band illuminants that are similar to the basis functions simplifies and improves accuracy of the computations. Each active illuminant 64 is modulated by a different orthogonal modulation control function $F_i(t)$, enabling separation of detector output from each active emitter (as described above) in step 26 of FIG. 2. In step 28 of FIG. 2, the surface reflectance function of the illuminated region of the scene is estimated from each individual active emitter output, thereby providing a higher accuracy than if only one active emitter were used.

Detector 56 is any device that can measure light reflected from a scene object. Examples of possible detectors include but are not limited to image sensors and photodetectors. Standard image sensors in digital cameras are CCD or CMOS arrays. In either case, each light sensing element integrates the incident light over the entire spectrum. In order to capture color images, a color filter array typically containing red, green and blue filter material is placed over the detector array. The image collected from the array is a mosaic of red, green and blue pixels, for example. Demosaicing algorithms are applied to the detector output to interpolate missing color values.

Figure 7:
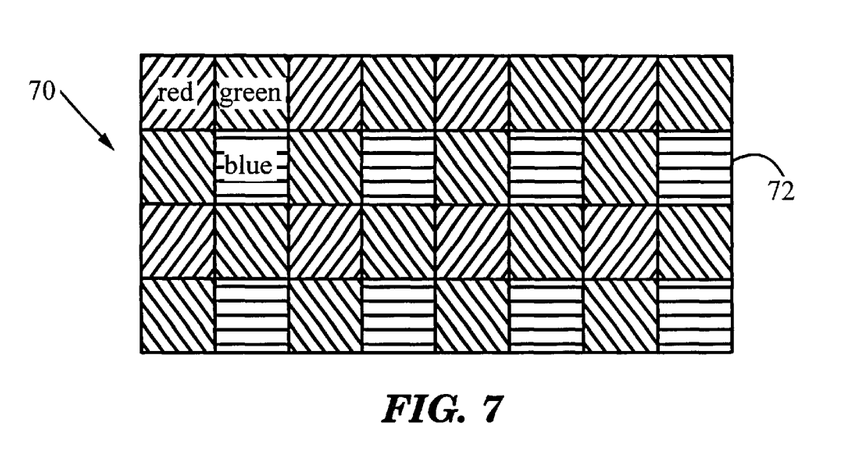
FIG. 7 is a block diagram of a detector of the apparatus of FIG. 5.

FIG. 7 is a schematic block diagram of one possible detector 70 containing multiple photodetectors 72, each with a color filter in its light path. Photodetectors 72 are identical to one another. By interposing color filters, each photodetector is made to detect a different spectral range. For example, the present invention can use standard mosaic patterns found in digital image detectors. Detector 70 of FIG. 7 uses a Bayer pattern, a common mosaic pattern used in still digital cameras. Any mosaic pattern can be used with the present invention. It is only important that the mosaic pattern is known for subsequent processing. Standard image processing techniques are used to obtain the $r(x,t)$ values from detector 70 necessary for performing demodulation as described above.

Processing means 58 perform the steps of method 20 of FIG. 2 described above, including separating emitter output from illuminant output, estimating the spectral surface reflectance function of the illuminated scene region, and estimating the spectral power distribution of the scene illuminant. Processing means 58 also control the modulation of the multiple illuminants of emitter 54 and synchronize emitter modulation with demodulation as necessary. Processing means 58 also perform the standard functions of processors in digital cameras or other image capture devices, such as compression, filtering, and demosaicing, as well as color balancing using the illuminant spectral power distribution estimated according to the present invention.

In conventional digital cameras, a variety of processing occurs when the shutter release button is partially depressed. For example, auto-focus and exposure measurements are acquired and processed before the image is acquired. The computations of the present invention are preferably also performed during this time. The emitter is activated, reflected light is detected, and processing is performed before an actual image is captured. The estimated illuminant properties are used for color balancing of the captured image or stored with the image for subsequent processing.

Preferably, apparatus 50 contains two detectors, a detector 56 used for performing the method of the present invention, and a separate image sensor for capturing images. Preferably, a small detector array is surrounded by emitter illuminants that illuminate only a small peripheral region of the scene. In this case, all computations are performed using output from detector 56 to obtain an illuminant spectral power distribution, which is stored in memory 60. Color balancing using the stored value is performed on images captured by the separate image sensor (passive images).

Alternatively, apparatus 50 contains only one detector, used both for acquiring passive images and for obtaining active measurements to perform the method of the present invention. In this case, color balancing is performed on either the illuminant output obtained by separating the total detector output into illuminant and emitter output or on images acquired when the emitter is not operating.

While the present invention has been described in reference to and is preferably implemented with digital imaging devices, it may also be used for color balancing of images acquired with film cameras. In this case, the identical steps are performed as described above, and the estimated illuminant spectral power distribution is used either to automatically provide color compensating filters during film exposure, or to encode the film with instructions to be used during developing. The invention can also be used with electric analog image sensors.

Although the present invention has been described in reference to and is preferably implemented with a temporal modulation, it may also be implemented using a spatially modulated active illuminant. For example, suppose the active illuminant falls upon a surface of spatially uniform reflectance. In this case it is possible to use the spatial variation across the image in a manner that is directly analogous to the temporal modulation of the active illuminant. The procedure in this case contains the following steps: A single image is acquired that includes both the passive and a superimposed spatially modulated active illumination. The spatial modulation of the active illumination is designed to be orthogonal to expected spatial variations of the passive illumination. Using procedures analogous to those of the temporal case, the light scattered by the active illuminant is distinguished from that scattered by the passive illumination, and the surface reflectance is estimated. Finally, the spectral power distribution of the passive illumination is computed using the estimated surface reflectance and the passive illumination image. In straightforward extensions, it is possible to create more sophisticated algorithms for analyzing inhomogeneous surface reflectance functions, as will be apparent to those of average skill in the art.

The method of the present invention can be incorporated into any device that uses knowledge of physical properties of scene objects or scene illuminants. For example, the present invention provides a remote light meter used to detect illuminant power at a particular location. Light meters are used in still and video photography to obtain information necessary for selecting camera exposure. Incident light meters measure the light intensity incident on the meter. Reflected or spot light meters estimate the light intensity reflected from a selected surface in a scene by assuming a value of the surface reflectance of the selected surface.

A remote light meter according to the present invention determines the illuminant power incident on a particular surface of a scene. The light meter contains an emitter and detector as described above. The device is operated by directing the emitter light toward a selected spot on a scene object and detecting the backscattered light. Using the method described above, physical properties of the scene illuminant such as spectral power distribution are determined. The light meter translates the measured power into the desired units and displays the measured value.

It will be clear to one skilled in the art that the above embodiment may be altered in many ways without departing from the scope of the invention. Accordingly, the scope of the invention should be determined by the following claims and their legal equivalents.

What is claimed is:

1. A method for estimating physical properties of a scene comprising a scene object illuminated by a scene illuminant, said method comprising:
    a) illuminating said scene with modulated light from an emitter, said modulated light having a predetermined spectral power distribution;
    b) detecting backscattered light from said scene using a detector;
    c) analyzing output from said detector to distinguish between illuminant output and emitter output, wherein said illuminant output represents backscattered light from said scene illuminant, and said emitter output represents backscattered light from said emitter; and
    d) estimating physical properties of said scene object in dependence upon said emitter output and said predetermined spectral power distribution.

2. The method of claim 1 wherein said physical properties of said scene object are related to a spectral surface reflectance function of said scene object.

3. The method of claim 1, further comprising estimating physical properties of said scene illuminant in dependence upon said physical properties of said scene object.

4. The method of claim 3 wherein said physical properties of said scene illuminant are related to a spectral power distribution of said scene illuminant.

5. The method of claim 1, further comprising performing color balancing on an image of said scene based in part on analysis of said output from said detector.

6. The method of claim 1 wherein said modulated light is temporally modulated light.

7. The method of claim 1 wherein said modulated light is spatially modulated light.

8. A method for estimating physical properties of a scene comprising a scene object illuminated by a scene illuminant, said method comprising:
    a) illuminating said scene with modulated light from an emitter, said modulated light having a predetermined spectral power distribution;
    b) detecting backscattered light from said scene using a detector;
    c) analyzing output from said detector to distinguish between illuminant output and emitter output, wherein said illuminant output represents backscattered light from said scene illuminant, and said emitter output represents backscattered light from said emitter; and
    d) estimating physical properties of said scene illuminant in dependence upon said emitter output and said predetermined spectral power distribution.

9. The method of claim 8 wherein said physical properties of said scene illuminant are related to a spectral power distribution of said scene illuminant.

10. The method of claim 8, further comprising performing color balancing on an image of said scene based in part on said physical properties of said scene illuminant.

11. The method of claim 8 wherein said modulated light is temporally modulated light.

12. The method of claim 8 wherein said modulated light is spatially modulated light.

13. An apparatus for detecting light in a scene comprising a scene object illuminated by a scene illuminant, said apparatus comprising:
    a) an emitter for emitting modulated light having a predetermined spectral power distribution;
    b) a detector for detecting backscattered light from said scene; and
    c) processing means for:
        i) analyzing output from said detector to distinguish between illuminant output and emitter output, wherein said illuminant output represents backscattered light from said scene illuminant, and said emitter output represents backscattered light from said emitter; and
        ii) estimating physical properties of said scene object in dependence upon said emitter output and said predetermined spectral power distribution.

14. The apparatus of claim 13 wherein said physical properties of said scene object are related to a spectral surface reflectance function of said scene object.

15. The apparatus of claim 13, further comprising processing means for estimating physical properties of said scene illuminant in dependence upon said physical properties of said scene object.

16. The apparatus of claim 15 wherein said physical properties of said scene illuminant are related to a spectral power distribution of said scene illuminant.

17. The apparatus of claim 13, further comprising processing means for performing color balancing on an image of said scene based in part on analysis of said output from said detector.

18. The apparatus of claim 13 wherein said emitter emits temporally modulated light.

19. The apparatus of claim 13 wherein said emitter emits spatially modulated light.

20. The apparatus of claim 13 wherein said apparatus is an imaging apparatus.

21. The apparatus of claim 13 wherein said apparatus is a light meter.

22. An apparatus for detecting light in a scene comprising a scene object illuminated by a scene illuminant, said apparatus comprising:
 a) an emitter for emitting modulated light having a predetermined spectral power distribution;
 b) a detector for detecting backscattered light from said scene; and
 c) processing means for:
  i) analyzing output from said detector to distinguish between illuminant output and emitter output, wherein said illuminant output represents backscattered light from said scene illuminant, and said emitter output represents backscattered light from said emitter; and
  ii) estimating physical properties of said scene illuminant in dependence upon said emitter output and said predetermined spectral power distribution.

23. The apparatus of claim 22 wherein said physical properties of said scene illuminant are related to a spectral power distribution of said scene illuminant.

24. The apparatus of claim 22, further comprising processing means for performing color balancing on an image of said scene based in part on said physical properties of said scene illuminant.

25. The apparatus of claim 22 wherein said emitter emits temporally modulated light.

26. The apparatus of claim 22 wherein said emitter emits spatially modulated light.

27. The apparatus of claim 22 wherein said apparatus is an imaging apparatus.

28. The apparatus of claim 22 wherein said apparatus is a light meter.

* * * * *